US00PP12504P2

(12) United States Plant Patent

Bessho et al.

(10) Patent No.: US PP12,504 P2

(45) Date of Patent: Apr. 2, 2002

(54) CALIBRACHOA PLANT NAMED 'COLORBURST CHERRY'

(75) Inventors: Masao Bessho, Kakegawa; Toshimi Ohga, Kikugawa, both of (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 09/400,366

(22) Filed: Sep. 21, 1999

(51) Int. Cl.[7] ..... A01H 5/00

(52) U.S. Cl. ..... Plt./263

(58) Field of Search ..... Plt./263, 356

(56) References Cited

PUBLICATIONS

Fehr, Walter R. Principles of Cultivar Development pp. 28–33, 86–87, 361–366.*

* cited by examiner

*Primary Examiner*—Bruce R. Campell

*Assistant Examiner*—Annette H. Para

(74) *Attorney, Agent, or Firm*—James R. Cypher; Charles R. Cypher

(57) ABSTRACT

A new Calibrachoa plant which combines a unique flower color, and a slightly mounding, vigorous growth habit with moderate branching. The plant grows vigorously, branches only moderately, and is appropriate as a hanging basket. Its flowers are funnel-shaped. The petals are united and each has a fissure and a slight indent. The flowers are axillary and solitary. Fully-opened flowers have a diameter between 2.6–3.2 cm. The throat and limbs of the petals are burgundy red (R.H.S. 64A red-purple group). The tube is light yellow (R.H.S. 9A). The plant is very resistant to rain, heat and drought. The plant grows and flowers best under low soil pH conditions (pH 5–6). Typically, flowers will stay open all day and night.

1 Drawing Sheet

BACKGROUND

This invention relates to a new and distinct cultivar of Calibrachoa plant, hereinafter referred to by the name 'Colorburst Cherry'. 'Colorburst Cherry' is a hybrid. In 1995, the inventors Masao Bessho, Seiji Nakamura, and Hitoshi Kojima crossed a variety obtained from a commercial market in South America with a patented hybrid at a commercial nursery in Kakegawa, Japan. The second generation progeny of this cross were found to have desirable characteristics, and the present invention was selected from this generation. The plant has been asexually reproduced through a number of generations since that time and its distinguishing characteristics have remain firmly fixed.

The Calibrachoa genus is a relatively new designation for a number of species that were formerly considered part of the Petunia genus.

The Petunia genus was originally established in 1803 by A. L. Jussieu, who described both *P. parviflora* Juss. and *P. nyctaginiflora* Juss. as type species. Using a non-horticultural system that selected the first mentioned species as the type species (lectotype), N. L. Britton and H. A. Brown declared *P. parviflora* Juss. as the type species for Petunia in 1913.

During the 1980's and 1990, H. J. Wijsman published a series of articles regarding the ancestry of *P. hybrida* (Hook.) Vilm., the Garden Petunia, and the inter-relationship of several species classified as Petunia. These studies discovered that *P. hybrida* (Hook.) Vilm. and its ancestral species, *P. nyctaginiflora* Juss. (=*P. axillaris* (Lam.) B.S.P.) and *P. violacea* Lindley (=*P. integrifolia* (Hook.) Schinz & Thellung.), possessed 14 pairs of chromosomes while several other species, including *P. parviflora* Juss., possessed 18 pairs of chromosomes. Since *P. parviflora* Juss. was the lectotype species for the Petunia genus, Wijsman and J. H. de Jong proposed transferring the 14 chromosome species to the genus Stimoryne. Horticulturists opposed reclassifying the Garden Petunia and in 1986, Wijsman proposed the alternative of making *P. nyctaginiflora* Juss. the lectotype species for Petunia and transferring the 18 chromosome species to another genus. The I. N. G. Committee adopted this proposal. By 1990 Wijsman had transferred several species, including *P. parviflora* Juss. (=*C. parviflora*) to Calibrachoa, originally established by Llave and Lexarza in 1825. *Calibrachoa parviflora* (=*C. mexicana* la Llave & Lexarza) is now the type species for the genus Calibrachoa.

Classification of the current Petunia and Calibrachoa species is still in progress. New species are also being identified. At present, Calibrachoa can be distinguished from Petunia based on the higher chromosome number, chromosome morphology, plant branching habit and type of flower bud aestivation.

To summarize a few of the more easily identified distinguishing characteristics: whereas Petunia species have 2n=14 chromosomes, Calibrachoa species have 2n=18 chromosomes. Whereas Petunia species bear a flower peduncle and one new stem from a node, Calibrachoa bear a flower peduncle and up to three stems. Finally, Petunia species have a cochlear corolla bud. A single outermost petal covers the other four petals which are radially folded and terminally contorted. Calibrachoa flower buds are flat with all five petals linearly folded. The two lower petals are fused together and form a cover around the three other petals.

Further information on the transfer of certain species of Petunia to Calibrachoa can found in the following articles which are incorporated by reference herein. H. J. Wijsman,

*On the Interrelationships of Certain Species of Petunia VI New names for the species of Calibrachoa formerly included into Petunia* (*Solanaceae*), Acta. Bot. Neerl. 39(1), 101–102 (March, 1990). H. J. Wijsman and J. H. de Jong, *On the Interrelationships of Certain Species of Petunia IV Hybridization between P. Linearis and P. Calycina and Nomenclatorial Consequences in the Petunia Group,* Acta. Bot. Neerl. 34, 337–349 (August, 1985). H. J. Wijsman, J. H. de Jong and T. M. Pedersen, *On the Interrelationships of Certain Species of Petunia III The Position of P. Linearis and P. Calycina,* Acta. Bot. Neerl. 32(4), 323–332, (August, 1983). Toshio ANDO, Yoshiro UEDA, and Goro HASHIMOTO, *Historical Survey and Present Status of Systematics in the Genus Petunia Jussieu* (*Solanaceae*), Technical Bulletin of Faculty of Horticulture, Chiba University, No. 45 (1992).

The new variety's female parent is a member of the Calibrachoa genus. No species determination of the female parent has been made. The female or seed parent is known to the inventors by its breeder code—C-13D. Parent C-13D was found in a commercial market in South America. It is characterized by reddish orange funnel-shaped flowers and an slightly mounding, erect growth habit.

The male plant crossed with C-13D was patented in the United States on May 6, 1997, by the same inventors. Its U.S. patent number is U.S. Plant Pat. No. 9,884. The inventors have named it 'Liricashower Rose'. Like the seed starter, its botanical classification has not been carried to the species level. In U.S. Plant Pat. No. 9,884, the genus for 'Liricashower Rose' was identified as Petunia. Since that time, as discussed above, the inventors have learned that the genus Petunia has been split by the I.N.G., and this particular variety, because of its chromosome number and bud aestivation is more accurately characterized as a member of the Calibrachoa genus. 'Liricashower Rose' is itself a hybrid plant, the result of a cross between plants obtained from commercial markets in South America.

The distinguishing characteristics of the 'Liricashower Rose' include bright funnel-shaped flowers, a decumbent growth habit and a large profusion of blooms. With regard to the color of the flowers, specifically, the throat and limbs of the petals are purple-rose (R.H.S. 74A at maturity) and the tube is white on its lower portion changing to light green-yellow tones on its upper portion.

The initial cross-pollination of the C-13D and 'Liricashower Rose', resulting in first generation seed, was made in June of 1995. This first generation seed was sown and yielded 20 plants. From these 20 plants, three plants were selected and intercrossed in a diallel pattern to produce second generation seed. In February of 1996, the second generation seed was sown and yielded 50 plants. From these 50 plants, seven plants were selected for their appealing flower color and decumbent growth habit. In February of 1997, the seven selected plant lines were vegetatively propagated and tested for ease of reproducibility and stability of traits. The present variety was selected from the seven for its vigorous growth, decumbent habit and burgundy red flower color.

In December of 1997, cuttings of 'Colorburst Cherry' were sent to a commercial nursery in Salinas, Calif. During the spring and summer of 1998, plants were grown under the direction and supervision of the inventors for evaluation of stability of the line's desired traits. Plants were grown in hanging pots at the commercial nursery in Salinas, Calif., and in cultivated fields at the commercial nursery in Kakegawa, Japan. Vegetative propagation in Japan was done in Kakegawa, Japan. The terminal 1.0 to 1.5 inches of an actively growing stem is excised. The basal half is stripped of leaves and dipped in a 1:19 dilution of Dip-N-Gro rooting solution (solution:water). The dipped potion of the stem is then inserted into moist peat-based soilless plant growing media. Soil trays with 1.0 inch diameter by 1.5 inch deep cells are used. The cuttings are kept in a warm greenhouse under a clear plastic tent with occasional misting from and automatic system. After about four weeks the cuttings have grown roots, bound together the soil as a root ball and can be transplanted to pots. Two generations of successive propagation (December 1997 and December 1998) were performed between the final selection and collecting data for the application. Vegetative propagation in Salinas, Calif. was performed in greenhouses at the Sakata Seed America Plug & Propagation facility. It takes approximately four weeks to produce a root cutting. 'Colorburst Cherry' was determined by the inventors to have its characteristics, as herein described, firmly fixed.

'Colorburst Cherry' is a new variety of Calibrachoa plant having a compact and slightly mounding growth habit. The plant grows vigorously and makes an excellent hanging basket. Its flowers are funnel-shaped. The petals are united and each has a fissure and a slight indent. The flowers are axillary and solitary. Fully-opened flowers have a diameter between 2.6–3.2 cm. The throat and limbs of the petals are burgundy red (R.H.S. 64A red-purple group). The tube is light yellow (R.H.S. 9A). The plant is very resistant to rain, heat and drought. The plant grows and flowers best under low soil pH conditions (pH 5–6). Typically, flowers will stay open all day and night.

The new variety is distinguished from other Calibrachoa plants by the combination of its characteristics. It combines a unique flower color, and a slightly mounding, vigorous growth habit.

The closest commercial cultivar of which the inventors are aware is the petunia-like plant named 'Million Bells Cherry Pink'. The distinguishing characteristics which differentiate 'Colorburst Cherry' from 'Million Bells Cherry Pink' are:

| | 'Colorburst Cherry' | 'Million Bells Cherry Pink' |
|---|---|---|
| Growth Habit | Slightly Mounding | Mounding |
| Flower Color | Burgundy red (R.H.S. 64A) | Bright purple red |
| Flower Diameter | 31–35 mm | Smaller |
| Growth Rate | Very vigorous | Low vigor |

BRIEF DESCRIPTION OF DRAWINGS

The accompanying drawings serve by color photographic means to illustrate the new plant variety, 'Colorburst Cherry'. The colors are represented as true as possible using conventional photographic procedures.

DETAILED DESCRIPTION OF THE NEW PLANT

Figure 1:
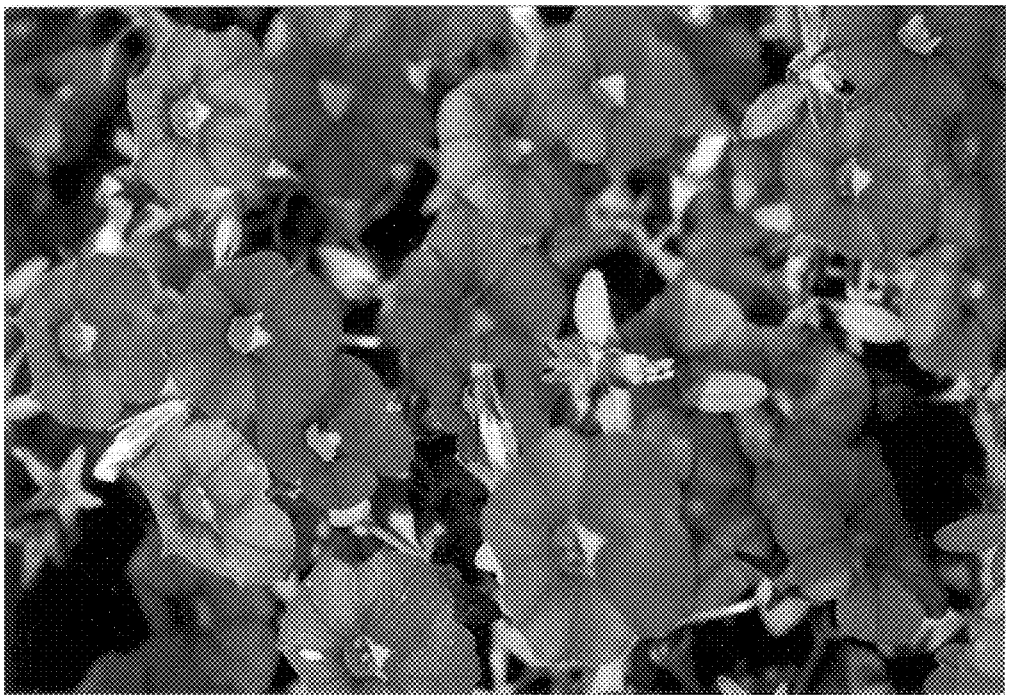
FIG. 1 is a close-up view of multiple blooms illustrating the color of the flowers and the large profusion of blooms.
Figure 2:
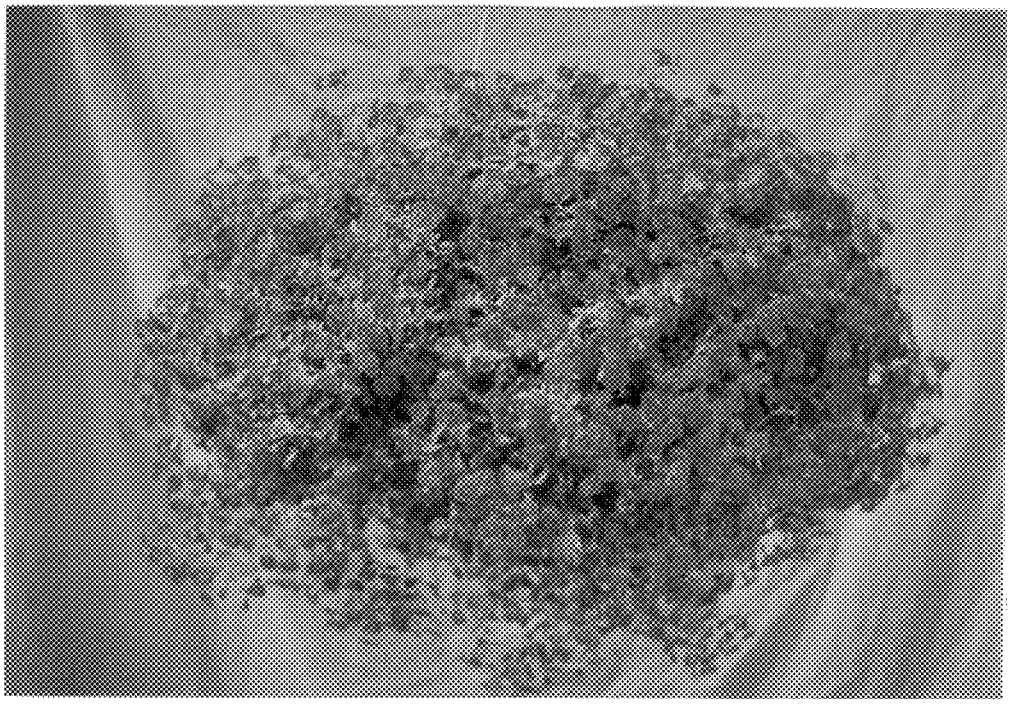
FIG. 2 is a view of the new cultivar after growing for several weeks in a hanging basket.

The following description is based on observations and measurements of plants grown in pots in Salinas, Calif. The plants were grown indoors. The plants received fertilizer water (constant liqued feeding) with an 18-8-8 feeding level. The plants had been growing for about 5 months since they had been transferred to their pot as rooted cuttings. The average growing temperature is 65 degrees Fahrenheit at night, and 75 degrees Fahrenheit in the day. Color designations were made according to The Royal Horticultural Society Colour Chart published by The Royal Horticultural Society of London, England.

Origin: Seedling.

Plants used for original crosses:

*Female.*—Unpatented and unnamed commercial market plant from South America, breeder code C-13D.

*Male.*—'Liricashower Rose' U.S. Plant Pat. No. 9,884.

Classification:

*Family.*—Solanaceae.

*Genus.*—Calibrachoa.

*Botanical.*—Unknown member of the Calibrachoa genus.

*Commercial.*—'Colorburst Cherry'.

Plant:

*Growth habit.*—Decumbent, slightly mounding in center.

*Plant height.*—18 cm.

*Spreading area of plant.*—28 cm. in all directions from the edge of the pot result from plants grown in a 41 cm. diameter hanging basket.

*Type.*—Perennial.

*Disease resistance.*—The plant is susceptible to Botrytis, powdery mildew, various stem and root rots, and certain viruses, like Tobacco Mosaic Virus and Impatiens Necrotic Spot Virus. Plants can be infested with aphids, leafminer, whitefly and various *Lepitopdera.*

*Blooming.*—Mature plants growing in a 41 cm. Diameter hanging basket can have in excess of 700 open flowers at any given time. The inflorescence is solitary.

Stem:

*Thickness.*—Main stem 2.0–3.0 mm.

*Color.*—Yellowish green (R.H.S. 143C).

*Pubescence.*—Stem pubescence is moderate in density and short. The pubescence is colorless and bulbous at the tip.

*Branching.*—Moderate.

*Length of internode.*—10–17 mm.

Leaf:

*Form.*—Alternate, elliptical with mucronate tips and entire margins.

*Length* (*average*).—22 mm.

*Width* (*average*).—8 mm.

*Thickness.*—0.5–0.8 mm.

*Color.*—The adaxial surface color of the leaves is R.H.S. 137C. The abaxial surface color of the leaves is R.H.S. 138B.

*Pubescence.*—Pubescence is short, colorless and bulbous at the tip.

Flower:

*Form.*—Flowers are axiallary and solitary. Flowers are bisexual. Calyx, corolla and androecium are all 5-parted. Calyx is persistent. Corolla is funnelform with 5 united petals. As flowers age the throat and limbs of the flower flare more abruptly. Petals have broad limbs, each petal is fissured with a slight indent.

*Diameter of corolla.*—26–32 mm when fully open.

*Tube length.*—15 mm.

*Throat diameter.*—8 mm.

*Color of petals.*—Young flowers: bright reddish purple (R.H.S. 63B).

*Color of petals in full bloom.*—When fully mature: the adaxial surface color of the limbs and throat is R.H.S. 61B and the adaxial surface color of the tube is R.H.S. 9A; the abaxial surface color of the limbs and throat is R.H.S. 63B and the abaxial surface color of the tube is R.H.S. 9C; the color of the flower petal vein is R.H.S. N187A.

*Reproductive organs.*—Androecium consisting of five stamens, 2 with long filaments bending upward over the pistil and 3 with short filaments, anthers are yellow and filaments are white. The color of the stamen is R.H.S. 160A. One pistil. Ovary is superior. Stigma is oval with a septation running through the middle on the long axis. The color of the ovary, pistil, style and stigma is R.H.S. 140C.

*Blooming habit.*—Flower stay open all day and night.

*Fragrance.*—The flowers of this plant do not possess any fragrance.

*Sepals.*—There are five sepals on each flower; the adaxial surface color of the sepal is R.H.S. 137C and the abaxial surface color of the sepal is 137C. Sepal pubescence is moderate in density, short, clear and bulbous at the tip. The sepals are fused at their base. Where they are not fused they taper in a lanceolate manner to an acute pointed tip.

Seeds/fruit: No seeds or fruit are produced.

*Blooming season.*—Plants flower April through October in Salinas, Calif.

Bud:

*Aestivation.*—Buds are flat with all five petals linearly folded and the two lower petals forming a cover around the three other petals. All the petals are fused together.

Chromosome number: 2n=18.

We claim:

1. A new and distinct variety of Calibrachoa plant as illustrated and described.

* * * * *